US005498244A

United States Patent [19]

Eck

[11] Patent Number: 5,498,244
[45] Date of Patent: Mar. 12, 1996

[54] SAFETY GUARD FOR MEDICAL INSTRUMENTS

[75] Inventor: Steven R. Eck, Broomall, Pa.

[73] Assignee: American Home Products Corporation, Madison, N.J.

[21] Appl. No.: 125,900

[22] Filed: Sep. 24, 1993

Related U.S. Application Data

[63] Continuation-in-part of Ser. No. 125,069, Sep. 22, 1993, abandoned.

[51] Int. Cl.$^6$ ..................................................... A61M 5/00
[52] U.S. Cl. ........................................... 604/198; 604/263
[58] Field of Search .................................. 604/110, 187, 604/263, 198

[56] References Cited

U.S. PATENT DOCUMENTS

| | | |
|---|---|---|
| 2,571,653 | 10/1951 | Bastien . |
| 4,356,822 | 11/1982 | Winstead-Hall . |
| 4,631,057 | 12/1986 | Mitchell et al. . |
| 4,655,751 | 4/1987 | Harbaugh . |
| 4,668,223 | 5/1987 | Grotenhuis . |
| 4,702,738 | 10/1987 | Spencer . |
| 4,737,144 | 4/1988 | Choksi . |
| 4,738,663 | 4/1988 | Bogan . |
| 4,747,837 | 5/1988 | Hauck . |
| 4,772,272 | 9/1988 | McFarland . |
| 4,790,827 | 12/1988 | Haber et al. . |
| 4,801,295 | 1/1989 | Spencer . |
| 4,804,372 | 2/1989 | Laico et al. . |
| 4,846,796 | 7/1989 | Carrell et al. . |
| 4,850,994 | 7/1989 | Zerbst et al. . |
| 4,871,355 | 10/1989 | Kikkawa . |
| 4,892,523 | 1/1990 | Haber . |
| 4,917,679 | 4/1990 | Kronner . |
| 4,923,445 | 5/1990 | Ryan . |
| 4,927,018 | 5/1990 | Yang et al. . |
| 4,946,447 | 8/1990 | Hardcastle et al. . |
| 4,947,863 | 8/1990 | Haber et al. . |
| 4,976,702 | 12/1990 | Andrews et al. . |
| 5,024,616 | 6/1991 | Ogle, II . |
| 5,201,721 | 4/1993 | Lee et al. . |
| 5,215,535 | 6/1993 | Gettig et al. . |

*Primary Examiner*—John D. Yasko
*Attorney, Agent, or Firm*—Steven R. Eck

[57] ABSTRACT

A sanitary or safety guard for a medical device subject to contamination, the medical device having a recess in its external surface, the guard comprising:

(a) an elongate, hollow guard body having an internal chamber, an internal surface, an external surface, a first opening, and a second opening, the first and second openings being located at opposite ends of the guard body, the first opening being sufficient to allow at least a portion of the medical device to enter into the internal chamber and the second opening being sufficient to allow a portion of the medical device to extend from the internal chamber through the second opening;

(b) a passage extending through the guard body between the internal and external surfaces;

(c) a biasing arm connected by hinging means to the guard body;

(d) an intrusion tab secured to the biasing arm such that the biasing arm projects the intrusion tab through the passage into the internal chamber of the guard body;

(e) locking means secured to the guard body such that the locking means are antagonistically disposed to the biasing arm, the biasing arm being movable between a first position in which contact between the intrusion tab and a medical device disposed within the internal chamber forces the biasing and in an arcing direction away from the guard body, a second position in which the biasing and is releasably located in close proximity to the locking means, and a third position in which the biasing arm is irreversibly secured by the locking means.

18 Claims, 6 Drawing Sheets

SAFETY GUARD FOR MEDICAL INSTRUMENTS

This application is a continuation-in-part of the application Ser. No. 08/125,069 entitled "Safety Guard for Medical Instruments" filed on Sep. 22, 1993, now abandoned.

FIELD OF THE INVENTION

This invention pertains to devices designed to protect practitioners from undesirable contact with medically related instruments. More particularly, the present invention relates to guards or shields which prevent medical practitioners from accidental contact with the needles or blunt cannulas of syringes and blood-collecting tubes.

BACKGROUND OF THE INVENTION

Increased concerns over diseases transmitted via bodily fluids, such as Acquired Immune Deficiency Syndrome (AIDS) or Hepatitis B, have dramatically increased the search for methods and means of preventing their spread. In the last decade this has led to the development of dozens of devices designed to decrease the incidence of accidental contact with contaminated medical sharps, such as the needles of used syringes. While these devices demonstrate at least minimal utility, many of them have designs which are unnecessarily complicated, require alterations to the instruments with which they are used, or are limited in their degree of protection.

Among the guards or shields disclosed for use with medical syringes are those found in U.S. Pat. Nos. 4,631,057 (Mitchell), 4,737,144 (Chokai), 4,871,355 (Kikkawa), and 4,946,447 (Hardcastle et al.).

The Mitchell patent discloses a tubular needle guard which can be telescoped over a collar mounted on a syringe to a position in which the guard protectively covers the syringe's needle. The Mitchell device's requirement of a separate collar adds critical internal and external dimensional requirements as well as unnecessary production steps and costs.

U.S. Pat. No. 4,737,144, issued to Chokai, teaches a similar tubular syringe needle guard which telescopes over the surface of a syringe until retention means, associated with the guard and the syringe's barrel, lock the guard in an extended position covering the syringe's needle. While the Chokai device does not require the collar associated with the Mitchell invention, it is only useful with specifically engineered syringes. Such syringes must have an annular slot towards the rear of the syringe barrel to receive the guard's retention means while the guard is in its retracted position, as well as an accompanying ramp intersecting the annular slot to guide the retention means from the slot. Furthermore, the locking mechanism disclosed by Chokai requires a specific, sharply angled type of annular recess to retain the guard in its extended position. Since the Chokai locking mechanism is designed to slide on the ramp associated with the rear annular slot, it would not secure the guard to syringes having more gradually sloped forward surfaces.

U.S. Pat. No. 4,871,355, issued to Kikkawa, provides a telescoping needle protection chamber for use with blood collection tubes. This chamber is designed to telescope along a needle-bearing blood collection tube between a first position in which the needle is exposed and a second in which the needle is within the protection chamber, with the chamber being releasably locked in each position. The Kikkawa releasable locking system allows an operator to manually move the protection chamber relative to the collection tube by applying a manual sliding force in the desired direction. While this allows easy and flexible operation, the lack of a more secure means of maintaining the protection chamber in the second position creates a potential for unintended exposure of used needles and accidental needle sticks.

U.S. Pat. No. 4,946,447, issued to Hardcastle et al., discloses a syringe-protecting sleeve which comprises a body split such that it has a longitudinal slit or aperture extending its entire length. This split body is snapped onto a syringe and may be slid over the syringe in a telescoping manner to cover the syringe's needle. This split guard also comprises a tab means which, when the guard is extended over the needle, contacts an axial wall at the distal end of the syringe to prevent the guard from sliding back along the syringe body to expose the needle. Such a design may be unsatisfactory for two reasons, the first being that the slightly greater than semicircular design may allow the guard to be removed unexpectedly or allow small fingers to pass through the longitudinal opening to contact the needle. In addition, the locking mechanism disclosed, like that of the Chokai invention, is designed to work with an axial wall and would not be effective with syringes having more gradually sloped forward surfaces.

In view of the limitations of the prior art, there continues to be a need for relatively uncomplicated needle guards that are useful in protecting against accidental punctures. There is a further need for such safety devices which do not require modification of already existing instruments, such as conventional syringes or preprepared syringe cartridges.

SUMMARY OF THE INVENTION

The present invention provides a guard or shield which may be used to increase the safety of instruments which have sharp or contaminated surfaces. Such instruments include those potentially dangerous instruments found in both the home and in industrial settings. More particularly the present invention provides a guard or shield which may be used upon medically related instruments, for example syringes, blood-collection tubes, scalpels, trocars, lancets, bistouries, intravenous needles and cannulas, biopsy needles and devices, to prevent unintended contact with their needles, blades, etc. For the purposes of this disclosure, the medically related instruments and syringes in question are intended to include those used for medical, dental, veterinary and all other life science, as well as those having other scientific or technical uses. Of particular interest is the present invention's ability to provide a guard to cover the needles or blunt cannulas of syringes and needle-bearing fluid collecting tubes, such as those used to collect blood. Due to the significant similarities in the shape and design of the tubular bodies and attached needles of syringes and needle-bearing blood collection tubes, references herein to syringes are intended to include the syringe-like blood collection tubes.

In general, the present invention may be described as follows:

A sanitary guard for a medical device subject to contamination, the medical device having a recess in its external surface, the guard comprising:

(a) an elongate, hollow guard body having an internal chamber, an internal surface, an external surface, a first opening, and a second opening, the first and second openings being located at opposite ends of the guard body, the first opening being sufficient to allow at least a portion of the medical device to enter into the internal chamber and the second opening being sufficient to allow a portion of the medical device to extend from the internal chamber through the second opening;

(b) a passage extending through the guard body between the internal and external surfaces;

(c) a biasing arm connected by hinging means to the guard body;

(d) an intrusion tab secured to the biasing arm such that the biasing arm projects the intrusion tab through the passage into the internal chamber of the guard body;

(e) locking means secured to the guard body such that the locking or latching means are antagonistically disposed to the biasing arm, the biasing arm being movable between a first position in which contact between the intrusion tab and a medical device disposed within the internal chamber forces the biasing arm in an arcing direction away from the guard body, a second position in which the biasing arm is releasably located in close proximity to the locking or latching means, and a third position in which the biasing arm is irreversibly secured by the locking means.

The present guard is intended to protect practitioners of activities requiring the use or disposal of the device in question, which may become contaminated by any manner, such as contact with contaminated fluid or tissue. It is preferred that the first and second openings and the internal chamber be of those dimensions which allow the internal dimensions of the guard to move over and in close proximity to the external dimensions of the medical device between a first position in which a portion of the medical device extends from the internal chamber through the second opening and a second position in which the guard has been advanced to cover the portion of the medical device previously extended through the second opening. In the cases of many conventional medical devices, such as scalpels, syringes, blood collection tubes, etc., the guard body will have substantially the same overall shape as an enlarged version of the devices external shape. In these instances, the guard will be substantially coaxial to the medical device and be easily telescoped between positions on the device. It is also preferred that the locking or latching means be capable of securing the biasing arm in the third position such that the biasing arm cannot be removed absent an exceptional or extraordinary action.

In a more specific description, the present invention consists of a guard for syringes, the guard comprising:

(a) an elongate, hollow guard body having openings at each end and internal dimensions sufficient to allow the guard body to telescope over a syringe between a first position in which the distal end of the syringe is exposed and a second position in which the guard body extends beyond and inhibits contact with the distal end of the syringe;

(b) said hollow guard body providing a biased member, the biased member comprising a biasing arm and an intrusion tab, such that the biased member is put in contact with the external surface of a syringe barrel when the guard is in its first position and the biased member is depressed into a recess in the syringe's surface when the guard is in its second position; and (c) means of securing the biased member in the recess such that the guard is maintained in the second position.

Of particular interest is the present invention's ability to releasably retain the guard in its second position and its ability to secure the guard in the second position when desired. In a more specific description, the present invention comprises:

More specifically still, this invention provides a syringe guard for use with a syringe, the syringe having a proximal end and a distal end, an external surface, a recess in the external surface, and nozzle means attached to and extending from the distal end of the syringe, the syringe guard comprising:

a) a tubular guard body having open proximal and distal ends, the open proximal end having sufficient dimensions to allow the syringe to pass through the proximal opening, external and internal surfaces, and an interior chamber passing between the open proximal and distal ends, the interior chamber having dimensions sufficient to allow the syringe to pass through the tubular guard body between the proximal and distal ends such that the syringe guard telescopes over the external surface of the syringe between a first position in which the nozzle means is exposed and a second position in which the syringe guard extends over and beyond the nozzle means;

b) the guard body having a passage, the passage extending through the guard body's external and internal surfaces, in which is positioned retention means comprising a biasing arm terminating in an inwardly projecting intrusion tab, the biasing arm being secured to the guard body by hinging means, the intrusion tab having dimensions which allow the biasing arm to reversibly introduce the intrusion tab through the passage between the external and internal surfaces of the tubular guard body into the recess in the external surface of the syringe;

c) the guard body having locking or latching means antagonistically disposed to said biasing means and intrusion tab for securing the intrusion tab in the recess in the external surface of the syringe; the retention means provide manually operable locking means being attached to the tubular guard body in positions which allow the intrusion tab to be introduced into and secured into the recess in the external surface of the syringe when the syringe guard is in the second position.

For the purposes of these descriptions, the nozzle means is intended to include any nozzle, hub or other structure which secures or may be used to secure a needle or blunt cannula to the distal end of the syringe or blood collection tube.

An even more specific description of some of the syringe guards of the present invention is as follows:

A syringe guard for use with a syringe, the syringe having among its components a syringe body having a proximal end and a distal end, an external surface, a recess in the external surface, the recess being annular or non-annular, a nozzle means attached to and extending from the distal end of the syringe body, the nozzle means securing a syringe needle or blunt cannula to the distal end of the syringe, the syringe guard comprising:

a) a tubular guard body having open proximal and distal ends, external and internal surfaces, and an interior space passing between the open proximal and distal ends, the interior space allowing the syringe to pass through the tubular guard body between the proximal and distal ends such that the guard body is telescopically slidable over and in close proximity to the external surface of the syringe between a first position in which the syringe needle or blunt cannula is exposed and a second position in which the syringe guard extends over and beyond the syringe needle or blunt cannula;

(b) a biasing arm and an intrusion tab, the biasing arm having one end connected to the guard body by hinging means and an unconnected end, the unconnected end either having or not having a locking protrusion extending therefrom, the intrusion tab having dimensions which allow the biasing arm to reversibly introduce the intrusion tab through a passage between the external and internal surfaces of the guard body such that, when the guard is in the first position, the intrusion tab contacts the external surface of the syringe body and, when the syringe guard is in the second position, the intrusion tab is releasably introduced into the recess in the external surface of the syringe;

(c) locking or latching means secured to the guard body in a position antagonistically disposed to the unconnected end of the biasing arm and/or the locking protrusion for securing the intrusion tab in the recess in the external surface of the syringe body when the syringe guard is in the second position, the manually operable locking or latching means being either an adjacent portion of the guard body under which the unconnected end of the biasing arm or the locking protrusion may be depressed and secured to maintain the intrusion tab in the recess or an adjacent securing means which provides a locking channel into which the unconnected end of the biasing arm or the locking protrusion can be introduced and secured to maintain the intrusion tab in the recess.

In a more preferred description, the syringe guard would also contain one or more additional securing mechanisms which include the various possible combinations of the hinging means, biasing arm, intrusion tabs, locking protrusion, adjacent locking means, locking channel, adjacent portion of the guard body, or other means or components listed above.

BRIEF DESCRIPTION OF THE DRAWINGS

FIG. I provides a longitudinal, cross-sectional view of one of the present invention's syringe guards on a syringe, with the guard being in the first, retracted position to expose the syringe's needle.

FIG. II provides a longitudinal, cross-sectional view of the syringe in FIG. I in which the syringe guard has been advanced to its second position in which the syringe guard encloses and shields the syringe's needle.

FIG. III depicts a longitudinal, cross-sectional view of the syringe and guard shown in FIG. II in which the syringe guard has been locked or secured into the second position shielding the syringe's needle.

FIGS. IV–VI illustrate longitudinal, cross-sectional views of a preferred mechanism for securing the syringe guard in the retracted, reversibly secured and locked positions.

FIG. VII provides a three-dimensional side view of a blunt cannula syringe with which this invention is useful.

FIG. VIII provides a longitudinal, cross-sectional view of a syringe guard useful with a blunt cannula.

FIG. IX depicts a three-dimensional, top view of the syringe guard of FIG. VIII.

FIG. X provides a three-dimensional view of a syringe guard on a blunt cannula syringe in which the guard is in the first position exposing the blunt cannula.

FIG. XI provides a three-dimensional view of the syringe and guard of FIG. X in which the syringe guard has been advanced to its second position surrounding the syringe's blunt cannula.

FIG. XII illustrates a three-dimensional view of a needle-bearing syringe and a needle guard, both exhibiting particular embodiments of the present invention.

FIG. XIII illustrates a three-dimensional view of a safety guard of the present invention situated in a retracted position on the handle of a scalpel.

FIG. XIV further illustrates, in an expanded, three-dimensional view, the securing and locking mechanisms of the guard seen in FIG. XIII.

FIG. XV provides a longitudinal, cross-sectional view of a retention means for the present guards in relation to a syringe.

DETAILED DESCRIPTION OF THE INVENTION

Figure 1:
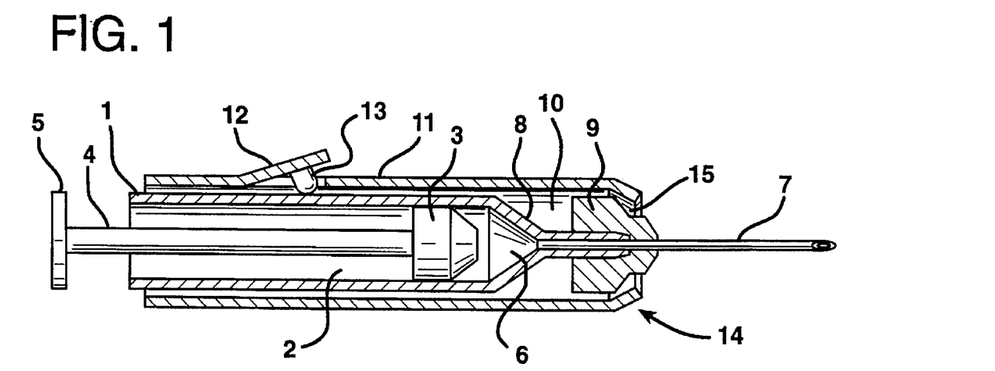
Figure 2:
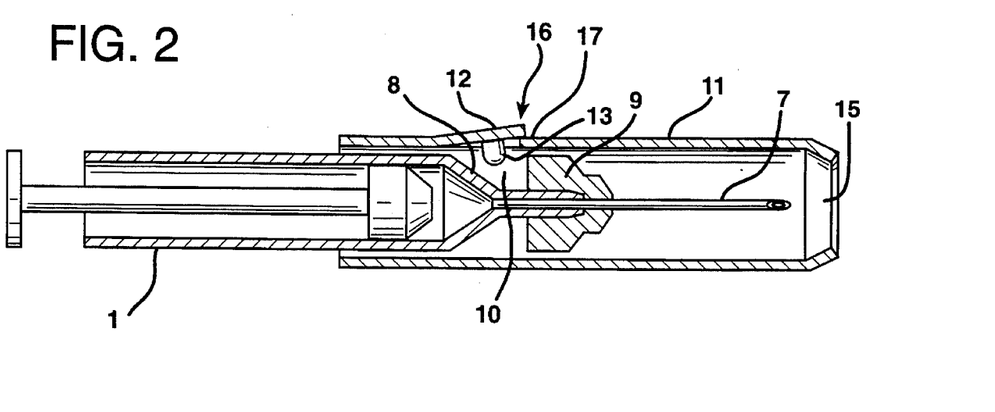
Figure 3:
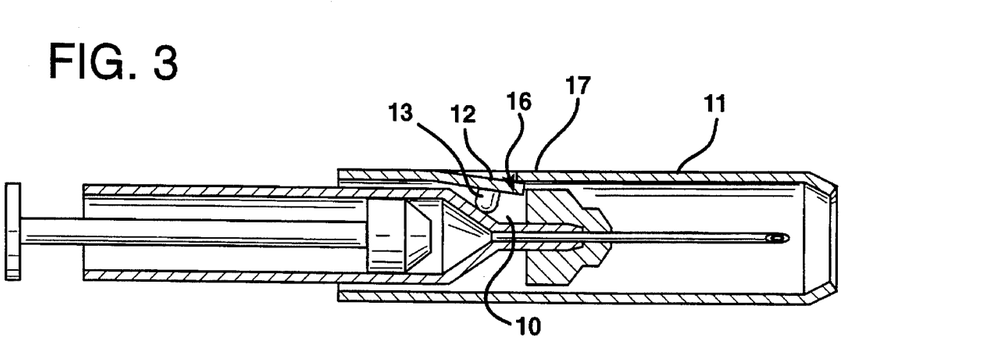
Figure 4:
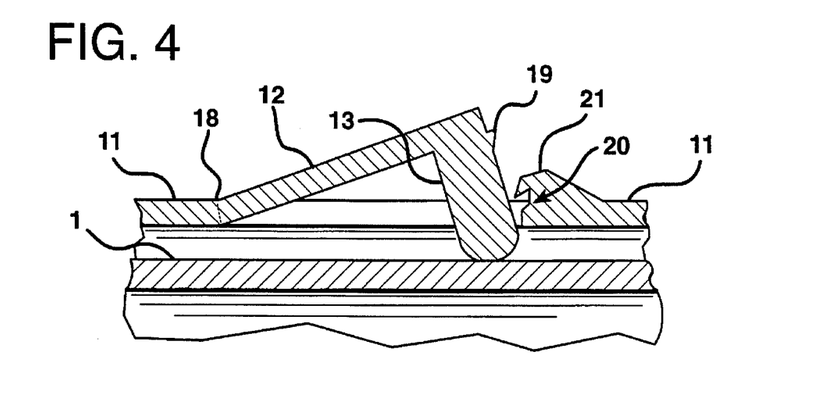
Figure 5:
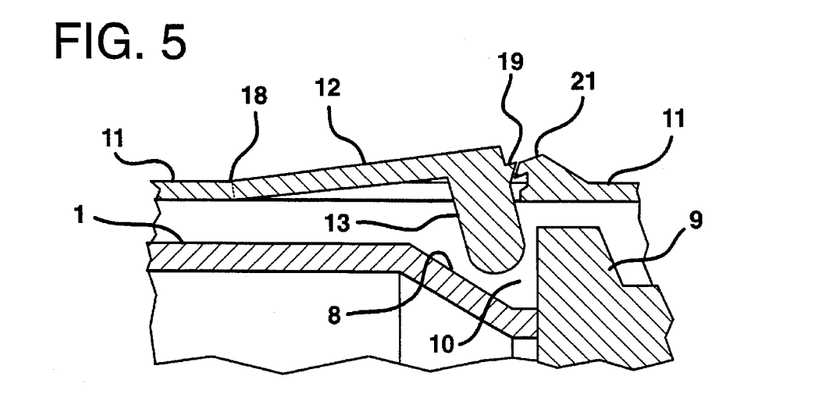
Figure 6:
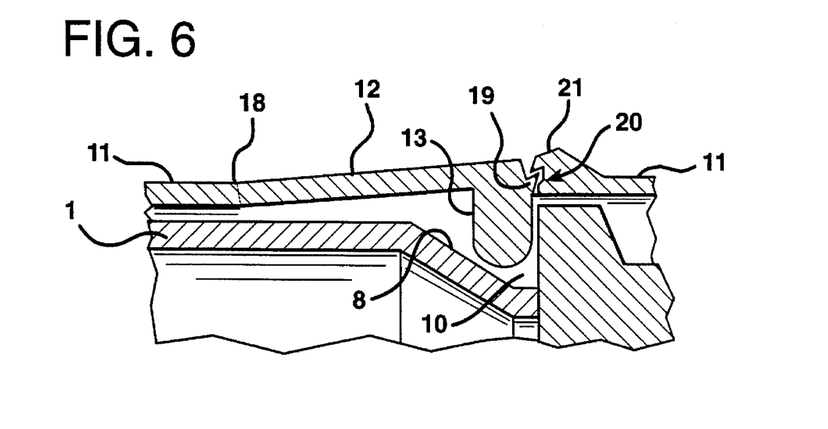
Figure 7:
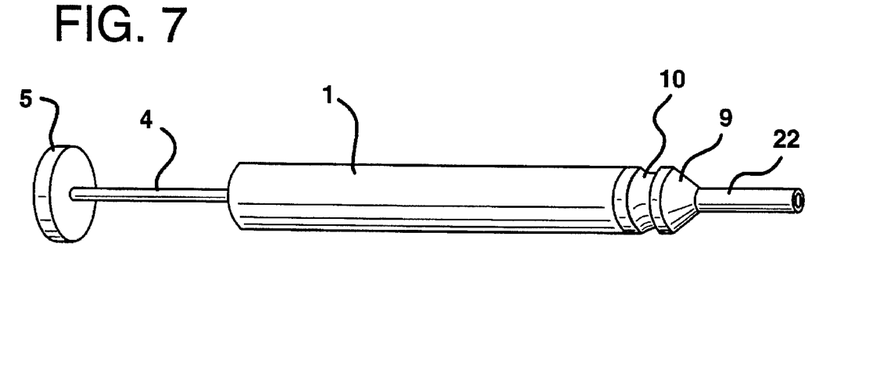
Figure 8:
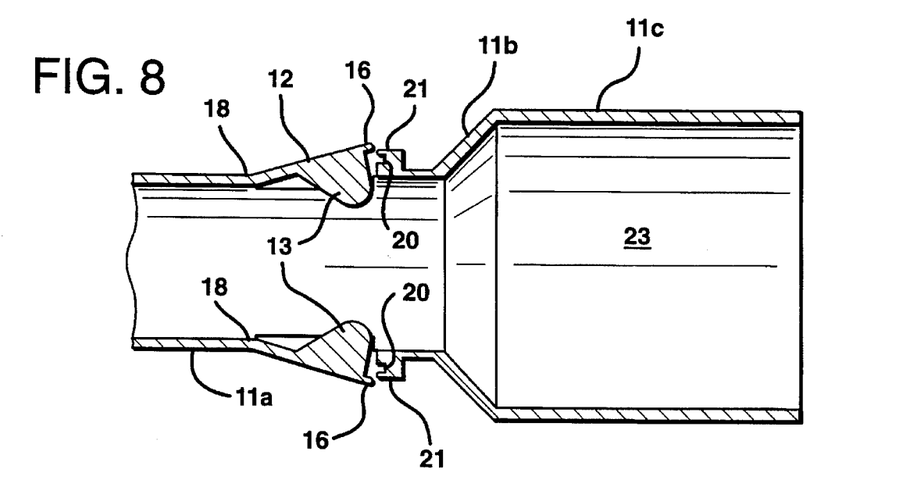
Figure 9:
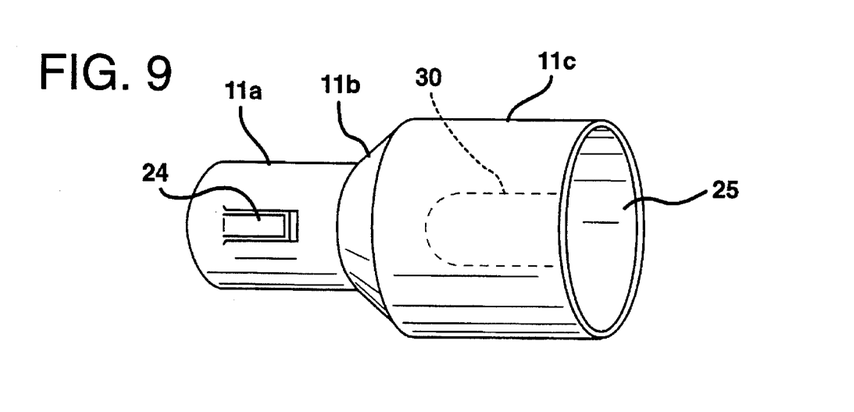
Figure 10:
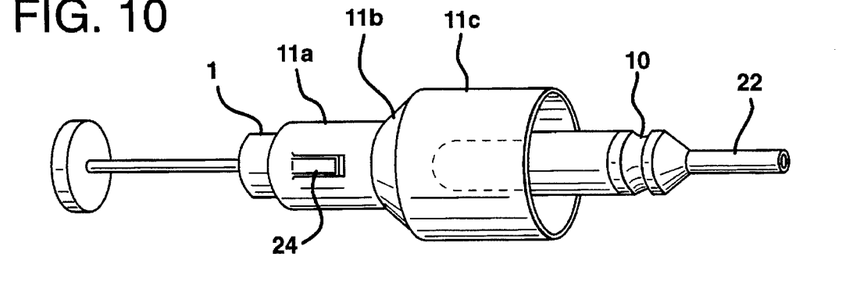
Figure 11:
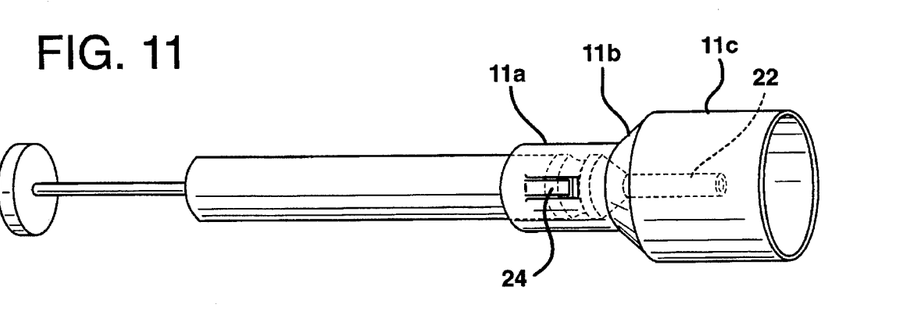
Figure 12:
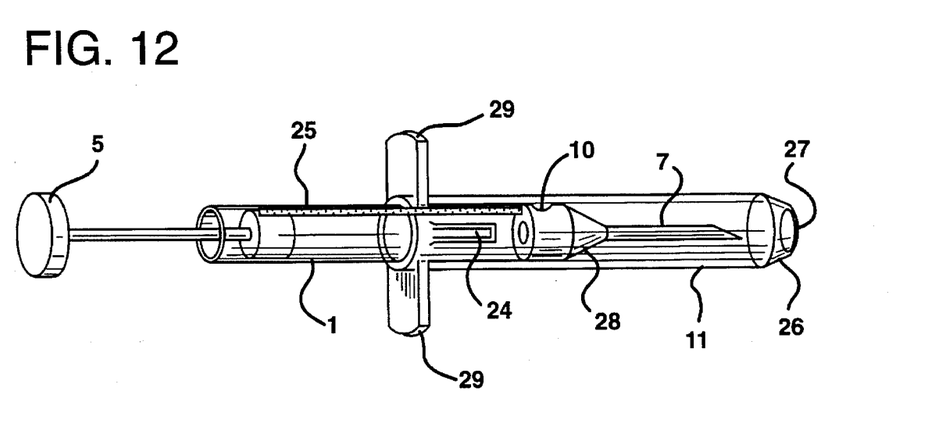
Figure 13:
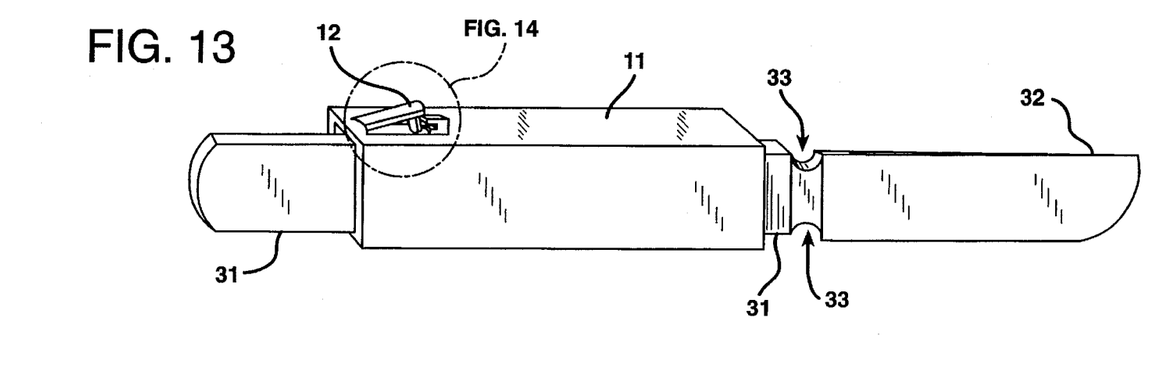
Figure 14:
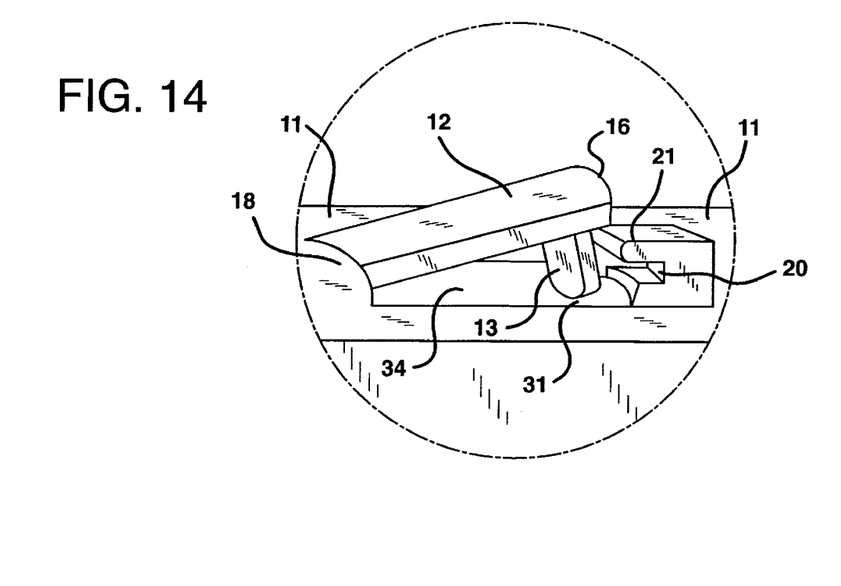
Figure 15:
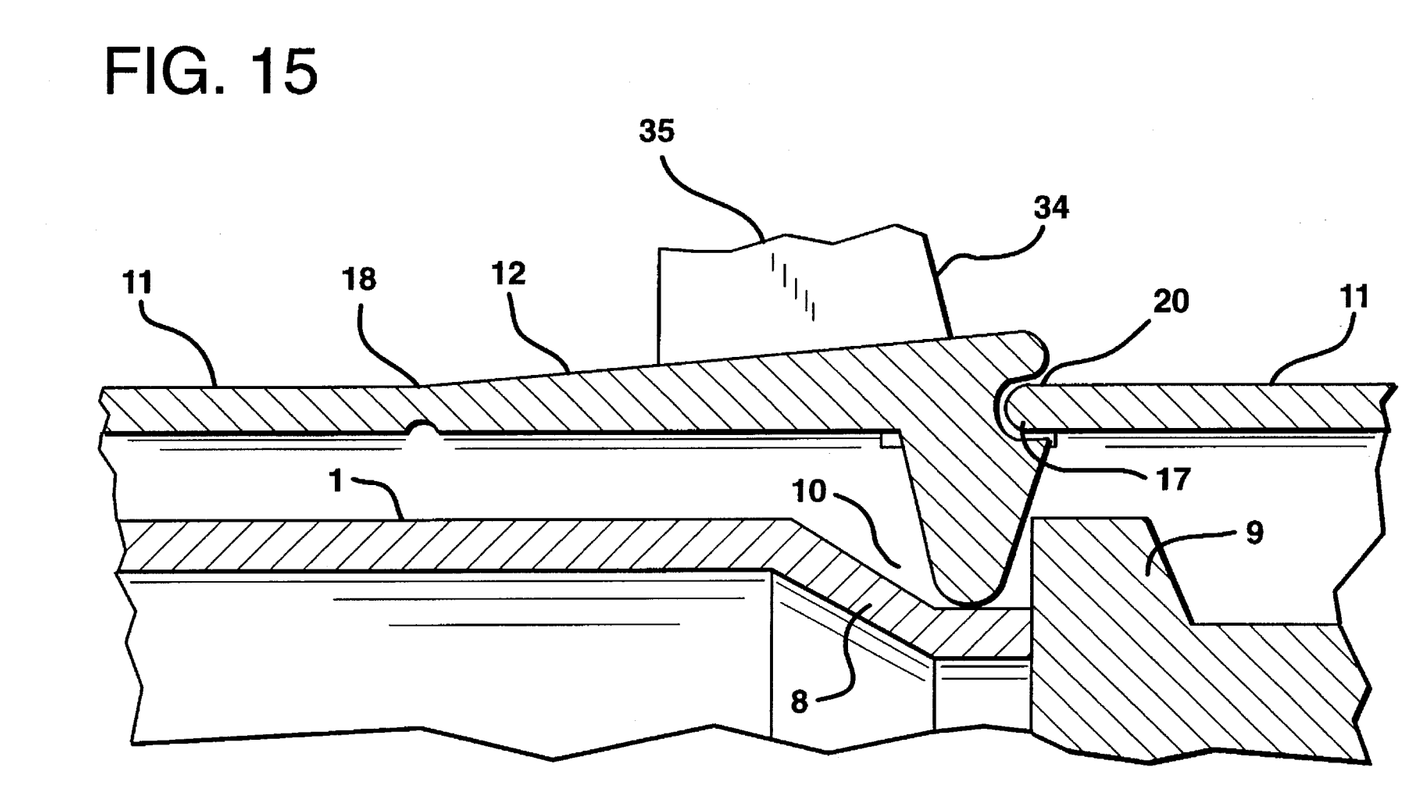

The present invention provides a means of protecting the users of medically related devices from unintentional contact with sharp and/or contaminated surfaces of the devices. More particularly, the invention provides a means of protection from the needle end of syringes or other needle-bearing devices. As the market is creating a need for needle-less drug delivery systems, the present invention also provides a means for shielding the cannula portion of a needle-less device, such as a blunt cannula-bearing syringe. FIGS. I–XII are helpful in describing the present invention and provide an understanding of some of its various embodiments.

FIG. I illustrates a cross-sectional view of a guard of the present invention mounted on a hypodermic syringe. The syringe, itself, comprises features familiar to those skilled in the art. It has a substantially tubular syringe body (1) defining an internal space (2) through which fluids are stored and passed. Also depicted is a plunger comprising the standard plunger diaphragm (3), plunger rod (4) and plunger handle (5). When the plunger is depressed into the internal space (2), the fluid is forced from the distal end (6) of the internal space (2) through the hollow syringe needle (7).

The syringe design used for illustration in FIG. I has a constriction (8) at its distal end where it contacts a hub (9) which secures and aligns the needle (7) with the distal end (6) of the syringe's internal space (2). This constriction (8) provides an annular recess (10) between the syringe body (1) and the needle hub (9). The syringe design depicted is similar to that of the Tubex® syringes sold by Wyeth-Ayerst Laboratories, Philadelphia, Pa. For the purposes of this disclosure, the term "annular recess" refers to a structure comprising a recess or depressed groove which is located, formed or otherwise disposed circumferentially around the body of a medical device, such as a syringe or blood collection tube. It is understood that the present syringe guards are capable of modification within the scope of this invention and that they are useful with any number of syringe designs which have a recess, annular or otherwise, within their external surface. It is also understood that the needle-bearing or blunt cannula-bearing blood collection tubes contemplated by the present invention are similar to the syringes mentioned above due to their (a) tubular bodies through which fluid materials may pass, (b) a recess in the external surface of the tubular body, preferably in the more distal half of the body, and (c) a hollow needle or blunt cannula attached to the distal end of the collection tube.

For the purposes of this disclosure, the proximal end of syringes or other medical instruments shall be that end of the instrument normally facing towards the operator at the time of use. The distal direction shall be that end of the instrument normally directed away from the operator or towards the patient during use, such as the needle of a hypodermic syringe.

The syringe guard of FIG. I comprises a substantially tubular guard body (11) having internal dimensions which allow it to slide telescopically over and in close proximity to the external surface of the syringe body (1) between a first position in which the guard body (11) is retracted towards the proximal end of the syringe body (1) such that the syringe's needle (7) is exposed for normal use and a second position in which the guard body (11) extends over and shields the needle (7) to prevent accidental needle sticks.

The present syringe guards have biasing means for securing the syringe guard in its second position. FIG. I depicts this biasing means as a biasing arm (12) and an intrusion tab (13). The biasing arm (12) is formed into or attached to the syringe guard body (11) in such a manner that it provides a force to direct the intrusion tab (13) in the direction of the syringe. Preferably the biasing arm is formed into the guard body such that the end of the biasing arm connected to the guard body creates a spring-action hinge tending to force the biasing arm into a prescribed position, preferably a position substantially axial to the longitudinal surface of the guard body. When the guard is placed over a syringe, as in FIG. I, the intrusion tab (13) is limited in the extent it may be depressed as it forcibly contacts the surface of the syringe body (1). When the syringe guard is in this first position, the force of the intrusion tab (13) on the syringe body (1) provides a useful frictional force that maintains the guard in its position relative to the syringe body (1). Though not necessary, it is understood that, within the scope of the present invention, additional means of securing the syringe guard to the syringe may be utilized. Such additional means could include means for causing friction between the guard and the syringe body, such as additional tabs or gasket materials extending from the syringe guard to contact the syringe body. They could also include means associated with the guard body which am designed to frictionally grasp the distal end of the syringe, the needle hub for example, when the guard is in its first position.

FIG. I also illustrates a constricted distal end (14) of the syringe guard body (11). When the syringe bears a needle (7), it is preferable to reduce the guard's distal opening (15) with such a constriction if the guard's natural, non-constricted diameter would make it possible for a small finger to enter into the distal opening (15) to contact the needle (7). The body of the syringe guard (11) may also be tubular, with no constriction at its distal end, and have sufficient length that will prevent a finger from entering the distal opening (15) to contact the needle. As most syringes are sold with an accompanying cannula cover or safety cap over their needle or blunt cannula, another preferred embodiment of the present guards is a distal opening (15) which has sufficient dimensions to allow the guard to be placed on the syringe and moved between the first and second positions while a safety cap is secured over the needle (7).

FIG. II depicts the same syringe/guard pairing of FIG. I with the syringe guard having been advanced to a second position in which the guard body (11) extends over and shields the syringe's needle (7) and the intrusion tab (13) is aligned with the syringe's annular recess (10). In this position and the action of the biasing arm (12) depresses the intrusion tab (13) into the annular recess (10) until the distal portion (16) of the biasing arm (12) contacts a physical barrier preventing the biasing arm's further inward motion. In FIG. II, this physical barrier comprises an adjacent portion (17) of the guard body (11). In this position, the intrusion tab (13) extends into the recess (10) to a position in which it will detainably contact the rear or proximal portion of the needle hub (9) if the guard moves forward in the recess and it will contact the constricted surface (8) of the syringe body (1) if the guard is drawn backwards. In this position the guard body (11) is secured by antagonistic contact between the intrusion tab (13) and the needle hub (9) such that the guard cannot be moved forward to a more distal position. It is understood that the intrusion tab is either (a) of sufficient dimensions such that can be depressed into the recess without becoming a physical barrier which prevents the guard's locking or latching means from operating or (b) is made of a material which allows it to flex or compress sufficiently in the recess to allow the locking or latching means to operate successfully.

From this position, though, the guard can be manually retracted backwards by a positive, backwards force on the guard body. This flexibility of operation allows the practitioner to quickly and safely advance the guard to its second position to maintain the uncontaminated integrity of an unused needle without taking the time necessary to retrieve and replace the safety cap originally covering the needle. Then the practitioner can retract the guard to its first position and use the syringe in normal fashion. The flexibility of the present system also allows a safer method of recapping the needle of an unused syringe. Rather than attempt to place the sharp end of an exposed needle into the narrow opening of the safety cap, the practitioner can simply extend the present syringe guard into its second, extended position and then slide the needle cap through the open distal end (15) of the guard body (11) over the needle (7).

The syringe guards of the present invention are further capable of being secured or locked into the second, needle-shielding position as a final protection to practitioners and others after the needle has been used or otherwise become contaminated. FIG. III illustrates one preferred locking or latching means for securing the guard in this second position. In this view, a practitioner has applied a force upon the biasing arm (12) sufficient to force the distal portion (16) of the biasing arm (12) below the adjacent portion (17) of the guard body (11). The biasing arm (12) in this embodiment is of sufficient dimensions and comprised of a flexible material, such as molded plastic, that allows the practitioner to easily press the biasing arm (12) into the position depicted where it cannot rise back beyond the adjacent portion (17) of the guard body (11). The arrangement depicted lockingly retains the intrusion tab (13) into the recess (10) and secures the guard in its second position.

FIGS. IV—VI provide an enlarged, cross-sectional view of a securing mechanism for the present invention. In these enlarged views, a guard body (11) surrounds a syringe body (1) in a telescoping manner. These figures also depict a biasing arm (12) attached to the guard body (11) by a hinging means (18). This hinging means (18) may be any structural assembly which attaches the biasing arm (12) to the guard body (11) and applies an arcing force upon the biasing arm (12) directed to force the intrusion tab (13) towards the interior space of the guard body and into the syringe's recess to carry out the prescribed securing functions. It is preferred that the entire syringe guard be a molded product, preferably of clear plastic material, such as the acrylic plastics or polyethylene plastics, and that the hinging means (18) be a continuous, molded connection between the flexible biasing arm (12) and the relatively stable guard body (11). Such moldings may be carried out by reaction injection molding to create a safety guard in which the guard body, hinging means, biasing arm, intrusion tab, locking protrusion, if present, and locking means comprise a single, molded unit. In this preferred case, the biasing arm (12) would be molded to naturally align substantially axially with the wall of the guard body (11) such that the locking mechanism of the guard naturally approaches, but does not complete, the securely locked position. An example of this molded alignment between the biasing arm and guard body can be seen in the arrangement depicted in FIG. V. Such a molded plastic design, however, is not limiting to the present invention. The present guards may be made of any material practicable. In the case of medical devices which are continually reused, following sterilization, it may be preferable to form the guard from a material not distorted by the heat of sterilization, such as created by convention autoclaving, or permeated by conventional sterilizing cleaning materials.

When a syringe is passed into the interior space of the guard body, contact between the syringe body (1) and the intrusion tab (13) would force the intrusion tab (13) and its connected biasing arm (12) into the raised position of FIG. IV. The tension created along the biasing arm (12), particularly at the molded hinging means (18), will maintain the frictional contact between the intrusion tab and the syringe surface (1). This action not only maintains the potential of the intrusion tab to enter into the recess, but also provides a frictional connection which maintains the guard in its first position without the need for the additional recess required by other needle shield devices.

FIGS. IV—VI also depict a preferred latching means for securing the guard in the second position. This means comprises a locking protrusion (19) which extends from either the intrusion tab (13) or, preferably, the biasing means (12) for a sufficient distance that allows it to be moved into and securely retained by a locking channel (20) in an adjacent securing means (21). As the intrusion tab arcs into the recess, as seen in FIG. V, the biasing arm (12) moves into a position in which the locking protrusion is closely associate with, and preferably contacting, the adjacent securing means (21). When the operator has completed the relevant procedure, the guard is locked into the second position by a manual depression of the biasing arm (12) which forces the locking protrusion (19) past the body of the adjacent securing means (21) into the locking channel (20), as seen in FIG. VI. The distal end of the biasing arm may become situated in a position in which it is secured by the securing means in many ways. The guard can be designed such that the securing means is moved from its original position by the forceful contact of the biasing arm's depression, to return to its original position after the biasing arm passes into the secured position. It is preferred that the securing means be a maintained in a stable position and that the biasing arm be made of a flexible material which allows it to flex along its length between the hinging means and the securing means such that the unconnected end of the biasing arm can be forced past the antagonistic portions of the securing means and extend itself fully into the secured position.

As depicted in FIGS. I–VI and VIII, any number of locking or latching means may be used with the guards of this invention. The extension which secures the biasing arm may be merely the unattached end of the biasing (12) arm or it may be a locking protrusion (19) of any shape or dimensions that suffices to hold the intrusion tab (13) in the desired position. As depicted in these figures, the adjacent securing means (21) may comprise any structure which holds the biasing arm and the attached intrusion tab into the recess of the medical device. The securing means may comprise a structure with a locking channel of any dimensions sufficient to receive and retain the unattached end of the biasing arm or a locking protrusion. As shown in FIGS. I–III, it may also comprise an unaltered section of the guard body (11) under which the unattached end of the biasing arm or a locking protrusion may be forced and secured.

As mentioned above, the hinge (18) of this invention may be of any construction which allows the biasing arm to operate in the lever-like manner previously described to force the intrusion tab through a passage in the guard body toward and into the internal chamber defined by the guard body. It may be a biased hinging device that originally separate from either the biasing arm or the guard body, or both. The present invention also includes guards in which the hinging means is not directly attached to the guard body (11), but rather to an extension of the guard body, such as the upraised finger flanges (29) seen in FIG. XII. In such guards, the biasing arm can pass over the guard body to a point at which its connected intrusion tab (13) passes through a passage in the guard body to either contact the medical device in the internal chamber or pass into a recess in the device.

It is preferred that the hinge be a continuous, molded connection between the biasing arm and the guard body such that the biasing arm is a projection of the guard body positioned in an opening in the guard body between the hinged area (18) and the adjacent securing means (21). The biasing arm may be a molded strip of material having the same thickness as the guard body. It may also have a thickness which is either less than or greater than the guard body, itself. The hinging means may also be equal to, less than or greater in thickness than the guard body itself or the biasing arm itself. If the material used to create the guard body and the biasing tab is undesirably rigid, the hinging means may comprise a continuously molded, but thinner, portion of material between the biasing arm and the guard body. If the material used to mold the guard device, at the thickness used for the guard body and biasing arm, is likely to allow the biasing arm to remain in an outwardly flexed position due to contact between the intrusion tab and the medical device, the hinging arm may comprise a thickened section of the material overlapping lesser thicknesses of both the guard body and the biasing arm. It is preferred, for the ease of mold design, that the biasing arm, hinging means and guard body all be of substantially the same thickness.

It is understood that the biasing arm may be a relatively narrow strip of material having a width which is, for example, less that 5% of the circumference of the guard body. The width of the biasing arm may be considerably wider, having, for example, a width of up to or exceeding about 25% of the circumference of the guard body. With wider biasing arms, one skilled in the art may diminish the portion of the biasing arm directly hinged to the guard body to allow the hinge to more easily bend when a syringe is entered into the guard body. It is also understood that the orientation of the locking means on the guard body may be altered within the scope of this invention. The hinged area may be distal on the guard body to the adjacent securing means or they may be aligned annularly to each other, separated by a biasing arm which is curved to approximate the circumferential curve of the guard body.

It is also understood that the intrusion tabs of the present invention record may be of any dimensions which fit into a recess in the medical device's surface. For smaller, non-annular recesses, the intrusion tab may comprise a short, thin column of material which may be introduced into the dimensions of the recess. For larger and/or annular recesses, the intrusion tab will preferably have larger dimensions to reduce the motion of the guard relative to the syringe when the guard is secured into the second position. As some conventional syringes have an annular recess between the syringe and a significantly smaller needle hub, one embodiment of the present invention comprises a guard with a relatively wide intrusion tab, for example having a width equal to or exceeding about 20% of the guard body's external circumference. It is further preferred that such a tab have an unattached end which is curved such that, at its most depressed position, the unattached, curved end contacts the curve of the recessed syringe surface along substantially the entire width of the intrusion tab. It is most preferred that the intrusion tab have a design that will not allow it to pass beyond the distal, upward slope of the syringe's recess. For most recesses, a flattened forward surface of the intrusion tab which projects downward approximately perpendicular to the biasing arm is preferred. For recesses which are not formed with a gradually sloping proximal surface, i.e. those not possessing a sloped proximal recess surface such as those depicted in FIGS. V and VI, it is preferred that the surface of the intrusion tab which contacts the recess's proximal surface be sloped, itself, to create an inclined, planar surface which assists the proximal, manual withdrawal of the intrusion tab from the recess. An example of this inclined, planar surface can be seen on the proximal side of the intrusion tabs (13) in FIG. VIII.

FIG. VII illustrates an example of a blunt cannula-bearing syringe with which the present guards are useful. Like the more common needle-bearing syringes previously described, it comprises a tubular syringe body (1), a plunger assembly, of which the plunger rod (4) and plunger handle (5) are depicted, and a recess (10). The distal hub (9) of the syringe, however, attaches a hollow, blunt cannula (22) rather than a syringe needle. Such blunt cannulas are designed to allow injections through valve-like ports into various systems which are already intravenously connected to a patient. Examples of such ports are the LifeShield® Prepierced Reseal Injection Sites of Abbott Laboratories, the Interlink® Injection Sites of Baxter, International, and the SAFSITE® Reflux Valves of Burron Medical Incorporated.

While the blunt cannula (22), itself, protects from accidental punctures, the accompanying guards of the present invention further prevent unintended contact with the medications from the syringe or bodily fluids that may become situated on the blunt cannula or which may become expelled from the valve into which the cannula (22) is inserted.

FIG. VIII provides a cross-sectional, longitudinal view of a preferred syringe guard for use with syringes having a blunt cannula (22). This view illustrates a guard which has two opposing latching means comprising hinging means (18), biasing arms (12), distal portions (16) of the biasing arms (12), adjacent securing means (21) and locking channels (20). The use of more than one latching means is preferred with the guards of the present invention, if the syringe's recess or recesses so allow. In addition to the increased ability to secure the guard into the second position, additional locking or latching means increase the frictional grip which maintains the guard in the first position along the syringe's body.

FIG. VIII also illustrates a guard body (11a–c) comprised of three distinct sections. The first (11a) tubular section has an internal diameter such that it telescopes over and in close proximity to the syringe's external surface to allow the latching means to function as described above. The guard body has a flared portion (11b) which opens the guard's internal space (23) to its greatest dimensions within the guard's expanded distal portion (11c). This expanded distal portion (11c) is designed to have a diameter small enough to inhibit accidental contact with a used blunt cannula, yet broad enough to allow the syringe to be inserted into a system port, such as those mentioned above, while the guard is in its extended second position. During such uses, the syringe would be directed so that the blunt cannula enters the system port while the expanded distal section of the guard (11c) surrounds the external dimensions of the port. By doing so, the extended guard not only creates a wall that inhibits expelled fluids from contacting the operator, but also creates a barrier which inhibits unintentional torsion of the syringe which may dislodge it from the port. The latching means of the guard may be secured into its locked position during these uses so that the operator need not place his fingers near the distal end of the syringe or guard prior to disposal.

FIG. IX provides a three-dimensional top view of the guard illustrated in FIG. VIII, particularly its latching means (24), which depicts a combination of the hinging means (18), biasing arm (12) and its distal portion (16), the adjacent securing means (21), locking channel (20), and intrusion tab (13) of FIG. VIII, and the three sections of the guard body (11a, 11b and 11c). Also depicted is the guard's distal opening (25) which allows the passage through which the external system's port may pass to contact the blunt cannula.

FIG. IX also depicts another embodiment of the syringe guard depicted in FIG. VIII which allows the guard to be used with various intravenous (IV) systems. Many IV systems have a Y-shaped structure, with one arm and the leg of the Y comprising a first tube which carries fluids from a source down to the patient. The other arm of the Y, often referred to as a "Y-site", generally comprises a short, raised second tube having one end formed into and creating a continuous conduit with the first tube and the other end forming an enclosure through which materials may be injected into the second tube to mingle with the fluids being gravitationally moved towards the patient. This arrangement provides an efficient means of adding materials to an IV system via a needle-bearing or blunt cannula-bearing syringe. However, syringes having guards or shields formed over their needle or blunt cannula may have difficulty in fitting into the Y-site as the shield encounters the first IV tube. In many cases, therefore, it is preferable to have an open longitudinal aperture or slot (30) in the side of the guard body (11c) which allows the first tube of the IV system to pass through the guard body (11c) while the syringe's needle or blunt cannula is inserted into the IV system's Y-site.

FIGS. X and XI illustrate the first and second positions of the syringe guard of FIG. IX on the blunt cannula syringe of FIG. VII. In FIG. X, the guard body (11a–c) is telescopically situated on the syringe body (1) in the guard's first position. The guard is maintained in this position by frictional contact between the one or more latching means (24) and the syringe body (1) to leave the blunt cannula (22) exposed. When the operator so desires, the guard body (11a–c) can be manually moved forward to the second position, depicted in FIG. XI, where the operator has the option of engaging the latching means (24) in the annular recess (10) to secure the guard in its forward position. As this particular guard design is intended to allow the blunt cannula to be used while covered by the guard, it is preferred that the guard be made of a transparent material, such as a transparent plastic material.

FIG. XII depicts two additional embodiments of the present invention, a guiding means for alignment of guards on syringes having non-annular recesses and an additional guard design. The first embodiment shown is the guiding means (25) which comprises a distinct line on the syringe body (1). This line, which is preferably of a color distinct from that of the rest of the syringe body (1), assists the operator in advancing the latching means (24) to a site-specific, non-annular recess (10). To engage the locking or latching means (24), the operator would simply rotate the guard body (11) until the latching means (24) is aligned with the distinct guiding means (25) and move the guard forward, maintaining the described alignment, until the locking means (24) engages the non-annular recess (10). It is most preferred that both the guiding means (25) and the latching means (24) have a color distinct from that of the guard body (11) or the syringe body (1).

FIG. XII also illustrates an additional syringe guard design for use predominantly with prefilled syringe cartridges, such as the Tubex ® Sterile Cartridge Units of Wyeth-Ayerst Laboratories, or other syringes lacking the finger flanges of most conventional syringes. Many of such units are designed for use with a separate injector, such as Wyeth-Ayerst's Tubex® Injector (U.S. Pat. No. 4,642,103), which has its own finger flanges. This second preferred embodiment of FIG. XII comprises a syringe guard which also provides finger flanges.

The guard comprises a tubular guard body (11) which is constricted at its distal end (26) creating a diminished distal opening (27) which prevents the syringe body's distal portion (28) from passing beyond the opening (27). When the guard is in its first position, the syringe's needle (7) or blunt cannula extends through the distal opening (27) where it can be directed towards a patient or associated equipment. As the operator depresses the syringe's plunger handle (5) to expel the syringe's contents, the restricted opening contacts the distal end (28) of the syringe and prevents it from passing further through the guard body (11).

The syringe guard of FIG. XII also comprises a latching or locking means (24), as described previously, and further comprises one or more finger flanges (29) to assist the operator in grasping the device while injecting the syringe's contents. While FIG. XII illustrates two opposing lateral finger flanges (29), it is understood that circling flanges or any other finger-accessible handles or other structures designed to allow the operator to grip the guard body are considered within the scope of this invention. Like those of the other embodiments of this invention, it is preferred that the guard body of this design be comprised of a substantially transparent material. It is also preferred that the guard body (11) have a length which, while the guard is in its first position, places the finger flanges (29) in a position at or near the proximal end of the syringe body (1). It is further preferred that the guard have two opposing latching means (24).

In order to aspirate the syringe in question, the technician can use two fingers to depress the opposing biasing arms to firmly grip the syringe body (1) between the guard's intrusion tabs or, in the case of guards having only one biasing arm, the technician can depress the single biasing arm to grip the syringe between the single intrusion tab and the opposing inner surface of the guard body. Then the technician may pull on the plunger handle (5) to complete the aspiration.

A related design of the present safety guards is depicted in FIGS. XIII and XIV, which illustrate a safety guard for use with a conventional scalpel. The guard is depicted in a first, retracted position on a scalpel, with the scalpel passing through the guards internal chamber. In this illustration, the scalpel comprises a scalpel shaft (31) or handle, with the scalpel blade (32) extended at the exposed, distal end of the scalpel. Between the scalpel shaft (31) and the scalpel blade (32) is seen a recessed connection (33) between the shaft and blade. It is understood that this recess may be in the blade or the shaft, or any connection between the shaft and blade, and the recess may be annular, as shown, or it may limited to a specific site on the scalpel. As with the other versions of the present guards presented above, this guard design can be moved forward to a second position in which the guard body (11) covers and shields the scalpel blade (32). Such designs for this type of guard may be subject to significant alteration within the scope of the present invention. For example, the guard body may be shortened to a length only long enough to cover the blade and a small portion of the distal end of the scalpel shaft while the guard is in the second position. Such a shortened guard could be moved to the proximal end of the shaft to allow the scalpel operator to grasp the distal end of the scalpel shaft without encountering the guard body. The guard body may also be lengthened to cover substantially the entire length of the scalpel shaft. In such instances, the guard body, itself can serve as a handle, with the practitioner grasping the guard body (11) rather than the scalpel's shaft (31).

FIG. XIV illustrates a magnified view of the guard securing means depicted in FIG. XIII. In this view, the biasing arm (12) is connected to the guard body (11) by hinging means (18), with the intrusion tab (13) extending through a passage (34) in the guard body (11) and contacting the surface of the scalpel shaft (31) to force the biasing arm (12) into the upraised position depicted. Also depicted is the adjacent securing or locking means (21), with its locking channel (20), into which the distal portion (16) of the biasing arm (12), or a locking protrusion (not shown), if present, may be forced to secure the intrusion tab (13) into the scalpel's recess (33) when the guard is in its second position.

FIG. XV depicts, in a longitudinal, cross-sectional view, another preferred mechanism of securing the present instrument guards in the desired position. As a modification of the locking or retention means depicted in FIGS. IV—VI, this embodiment utilizes a locking channel in the biasing arm or intrusion tab to enclose the opposing section of the guard body. FIG. XV presents, as the medical device in question, a syringe having a syringe body (1) which has a constriction (8) prior to entering a needle hub (9). This constriction (8) creates an annular recess (10) into which the intrusion tab (13) of the present invention can be introduced. This embodiment of the securing or retention means utilizes a biasing arm (12) connected to the guard body (11) by hinging means (18). As with the other embodiments described above, the lever action of the hinging means (18) on the biasing arm (12) forces the intrusion tab (13) towards the interior of the guard body (11). The embodiment illustrated in FIG. XV secures the intrusion tab (13) into the syringe's recess (10) by enclosing the opposing portion (17) of the guard body (11) in a locking channel (20) found in either the distal or unconnected end of the biasing arm (12), the intrusion tab (13), or a combination of both the unconnected end of the biasing arm and the intrusion tab. For the purposes of this disclosure, and the claims below, reference to a locking channel (20) in the biasing arm is intended to include such a channel in either the intrusion tab or a combination of both the biasing arm and the intrusion tab.

The retention means depicted in FIG. XV can be operated in the same manner as those securing means previously described. In the guard's first position, the intrusion tab (13) is in frictional contact with the surface of the syringe. The practitioner may then manually advance the guard in an axial, telescoping manner over the syringe until the guard reaches its second position. At the second position, the intrusion tab (13) is located in the recess (10) and a portion of the biasing arm (12) or intrusion tab (13) is in close proximity to or in contact with the opposing portion (17) of the guard body (11). In order to complete the operation of the retention means, the operator merely depresses the biasing arm (12) to a position in which the opposing section (17) of the guard body (11) is securely located within the locking channel (20), as depicted in FIG. XV. It is understood that, as depicted in FIGS. IV—VI, a locking protrusion may be utilized with the locking channel (20) seen in FIG. XV, with the locking protrusion being secured to opposing portion (17) of the guard body (11).

A final embodiment of the present guards depicted by FIG. XV is a finger grip (34) which allows a practitioner to more easily grasp and depress the biasing arm (12) of the retention or locking means. This finger grip may be any manner of raised or depressed surface associated with the manually available outer surface of the biasing arm (12) which allows an operator ready access to and control over the biasing arm. It is preferred that the finger grip (34) have an uneven surface (35) to frictionally facilitate the operator's grip on the biasing arm (12).

It is understood that the present invention may be subject to many alterations and is only to be limited by the legal limits of the claims presented below.

What is claimed:

1. A sanitary guard for a medical device subject to contamination, the medical device having a recess in its external surface, the guard comprising:
   (a) an elongate, hollow guard body having an internal chamber, an internal surface, an external surface, a first opening, and a second opening, the first and second openings being located at opposite ends of the guard body, the first opening being sufficient to allow at least a portion of the medical device to enter into the internal chamber and the second opening being sufficient to allow a portion of the medical device to extend from the internal chamber through the second opening;
   (b) a passage extending through the guard body between the internal and external surfaces;
   (c) a biasing arm connected by hinging means to the guard body;
   (d) an intrusion tab secured to the biasing arm such that the biasing arm projects the intrusion tab through the passage into the internal chamber of the guard body;
   (e) locking means secured to the guard body such that the locking means are antagonistically disposed to the biasing arm, the biasing arm being movable between a first position in which contact between the intrusion tab and a medical device disposed within the internal chamber forces the biasing arm in an arcing direction away from the guard body, a second position in which the biasing arm is releasably located in close proximity to the locking means, and a third position in which the biasing arm is irreversibly secured by the locking means.

2. The sanitary guard of claim 1 wherein, in the second position, the biasing arm is releasably located in contact with the locking means.

3. The sanitary guard of claim 1 wherein the medical device is a syringe.

4. The sanitary guard of claim 3 wherein the syringe has thereon a hypodermic needle.

5. The sanitary guard of claim 3 wherein the syringe has thereon a blunt cannula.

6. The sanitary guard of claim 1 wherein the medical device is a scalpel.

7. The sanitary guard of claim 1 wherein the guard body, hinging means, biasing arm, intrusion tab, and locking means further comprise a single, molded unit.

8. The sanitary guard of claim 1 further comprising a locking protrusion secured to the distal end of the biasing arm.

9. A safety guard for use with a syringe, the syringe having a recess therein, the safety guard comprising:
   (a) an elongate, hollow guard body having openings at each end and an internal chamber sufficient to allow the guard body to telescope over a syringe between a first position in which the distal end of the syringe is exposed and a second position in which the guard body extends beyond and inhibits contact with the distal end of the syringe;
   (b) said hollow guard body providing a biased member, the biased member comprising a biasing arm and an intrusion tab, such that the biased member is put in contact with the external surface of a syringe barrel when the guard is in its first position and the biased member is depressed into a recess in the syringe's surface when the guard is in its second position; and
   (c) means for securing the biased member in the recess such that the guard is maintained in the second position.

10. A safety guard for use with a syringe, the syringe having an external surface, a recess in the external surface, and a nozzle means, the safety guard comprising:
   a) a tubular guard body having open proximal and distal ends, external and internal surfaces, and an interior chamber passing between the open proximal and distal ends, the interior chamber being sufficient to allow the syringe to pass through the tubular guard body between the proximal and distal ends such that the syringe guard telescopes over the external surface of the syringe between a first position in which the nozzle means is exposed and a second position in which the syringe guard extends over and beyond the nozzle means;
   b) the guard body having a passage, the passage extending through the guard body's external and internal surfaces, in which is positioned retention means comprising a biasing arm terminating in an inwardly projecting intrusion tab, the biasing arm being secured to the guard body by hinging means, the intrusion tab having dimensions which allow the biasing arm to reversibly introduce the intrusion tab through the passage between the external and internal surfaces of the tubular guard body into the recess in the external surface of the syringe;
   c) the guard body having locking means antagonistically disposed to said biasing means and intrusion tab for securing the intrusion tab in the recess in the external surface of the syringe, the retention means providing manually operable locking means attached to the tubular guard body in positions which allow the intrusion tab to be introduced into and secured into the recess in the external surface of the syringe when the syringe guard is in the second position.

11. The safety guard of claim 10 wherein the guard body, hinging means, biasing arm, intrusion tab, and locking means further comprise a single, molded unit.

12. The sanitary guard of claim 10 further comprising a locking protrusion secured to the distal end of the biasing arm.

13. A syringe guard for use with a syringe, the syringe having among its components a syringe body having a proximal end and a distal end, an external surface, a recess in the external surface, a nozzle means attached to and extending from the distal end of the syringe body, the nozzle means securing a syringe needle or blunt cannula to the distal end of the syringe, the syringe guard comprising:

a) a tubular guard body having open proximal and distal ends, external and internal surfaces, and an interior space passing between the open proximal and distal ends, the interior space allowing the syringe to pass through the tubular guard body between the proximal and distal ends such that the guard body is telescopically slidable over and in close proximity to the external surface of the syringe between a first position in which the syringe needle or blunt cannula is exposed and a second position in which the syringe guard extends over and beyond the syringe needle or blunt cannula;

(b) a biasing arm and an intrusion tab, the biasing arm having one end connected to the guard body by hinging means and an unconnected end, the intrusion tab being secured to the biasing arm and having dimensions which allow the biasing arm to reversibly introduce the intrusion tab through a passage between the external and internal surfaces of the guard body such that, when the guard is in the first position, the intrusion tab contacts the external surface of the syringe body and, when the syringe guard is in the second position, the intrusion tab is releasably introduced into the recess in the external surface of the syringe;

(c) locking means secured to the guard body in a position antagonistically disposed to the unconnected end of the biasing arm for securing the intrusion tab in the recess in the external surface of the syringe body when the syringe guard is in the second position, the locking means being an adjacent portion of the guard body under which the unconnected end of the biasing arm may be depressed and secured to maintain the intrusion tab in the recess.

14. The syringe guard of claim 13 wherein the locking means comprises an adjacent securing means which provides a locking channel into which the unconnected end of the biasing arm can be introduced and secured to maintain the intrusion tab in the recess in the external surface of the syringe.

15. The syringe guard of claim 14 wherein the unconnected end of the biasing arm further comprises a locking protrusion.

16. The syringe guard of claim 13 wherein the locking means comprises a locking channel positioned within the biasing arm such that the biasing arm may be moved into a secured position in which the opposing portion of the guard body is enclosed within the locking channel.

17. The syringe guard of claim 13 wherein the guard body further comprises one or more finger flanges.

18. The syringe guard of claim 13 wherein the distal opening is more constricted than the proximal opening.

* * * * *